US008431055B2

United States Patent
Platt et al.

(10) Patent No.: US 8,431,055 B2
(45) Date of Patent: Apr. 30, 2013

(54) METHOD OF FORMING A TEXTURED CONDOM

(75) Inventors: William D. Platt, Lumberton, NJ (US); R. Christian Millar, Cream Ridge, NJ (US); Richard Grotyohann, Hillsborough, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 129 days.

(21) Appl. No.: 13/009,743

(22) Filed: Jan. 19, 2011

(65) Prior Publication Data

US 2012/0181726 A1    Jul. 19, 2012

(51) Int. Cl.
- B29C 41/14   (2006.01)
- B29C 41/20   (2006.01)
- B29C 41/22   (2006.01)

(52) U.S. Cl.
USPC ............ 264/132; 264/135; 264/255; 264/305

(58) Field of Classification Search .................. None
See application file for complete search history.

(56) References Cited

U.S. PATENT DOCUMENTS

| | | | | |
|---|---|---|---|---|
| 2,152,725 A * | 4/1939 | Auzin | ............................ | 264/132 |
| 2,288,840 A * | 7/1942 | Raiche | ........................... | 264/224 |
| 2,586,674 A * | 2/1952 | Lonne | ........................... | 128/844 |
| 3,809,090 A * | 5/1974 | Povlacs et al. | ................ | 604/347 |
| 4,840,188 A * | 6/1989 | Heidenfelder | ................ | 128/844 |
| 4,881,553 A * | 11/1989 | Grossman | ..................... | 128/844 |
| 4,919,149 A * | 4/1990 | Stang | ............................. | 128/842 |
| 5,109,871 A * | 5/1992 | Thornton | ...................... | 128/844 |
| 5,112,555 A | 5/1992 | Morelli et al. | | |
| 5,715,839 A | 2/1998 | Strauss et al. | | |
| 6,182,661 B1 * | 2/2001 | Solanki et al. | ................ | 128/844 |
| 6,651,667 B2 * | 11/2003 | Osterberg | ..................... | 128/844 |
| 2005/0076916 A1 * | 4/2005 | Barder | .......................... | 128/844 |
| 2008/0142021 A1 | 6/2008 | Hook | | |

FOREIGN PATENT DOCUMENTS

WO    WO 02/087477    * 11/2002

OTHER PUBLICATIONS

Notification of Transmittal of the International Search Report and the Written Opinion of the International Searching Authority from WIPO—International Searching Authority dated May 7, 2012.

* cited by examiner

*Primary Examiner* — Edmund H. Lee
(74) *Attorney, Agent, or Firm* — Frenkel & Associates, P.C.

(57) ABSTRACT

A method of manufacturing a condom having an open end and a closed end, wherein the method is comprised of the steps of coating a bare mandrel with a pattern of coating material to form visual stimulation means, and subsequently uniformly applying additional material over these patterns to complete the formation of the condom, and thereby create projections between the ends of the condom for stimulation.

17 Claims, 4 Drawing Sheets

METHOD OF FORMING A TEXTURED CONDOM

FIELD OF THE INVENTION

The invention is directed to a method of manufacturing a condom whereby the condom possesses one or more textured rings, spirals, dots, images, or raised surfaces with the intention of providing a "pleasure bump" or visual cue for increasing stimulation.

BACKGROUND OF THE INVENTION

There has developed around rubber latex a substantial industry for producing such articles as condoms, rubber gloves, surgical supplies, balloons, bathing caps and countless other articles. The articles are generally produced by dipping glass, porcelain or metal mandrels into natural rubber latex baths and subsequently coagulating and curing the thin film of latex, which adheres to the mandrel. Thicker films are obtained by repeating the dipping, coagulating and curing operations as desired. The films are stripped from the mandrels and may optionally be further cured at elevated temperatures.

Normally a condom is made of strong, fine rubber, fine animal membrane or a synthetic polymer such as polyurethane. Of necessity, in order to provide an acceptable level of tactile stimulation to the wearer, the condom must be quite thin. In general, it is elastically fitted to the male organ and during coitus remains stretch and taut.

The traditional methods of manufacturing a contraceptive, prophylactic or condom involve the so-called straight dipping or dip and dry techniques wherein a phallic shaped mandrel of predetermined size is, optionally coated with a coagulating agent, and dipped into a bath containing natural rubber latex or a solution of synthetic polymer such as polyurethane. The mandrel when dipped may be stationary or rotating about its longitudinal axis. The mandrel is then removed from the bath, dried and cured. This process can be repeated several times until a condom of the desired thickness properties are achieved. During dipping, the mandrel is immersed to a depth sufficient to yield the finished condom of desired length plus an additional distance to allow for rolling the sheath on itself for several turns in order to form a ring at the open end of the condom. Following a final cure, the formed condom may be coated with an anti-tack material such as talc, micro-porous solid particles, lubricants, slip agents, spermicides, deodorants, etc., prior to removal from the mandrel.

After completion of the dipping, ring-forming, curing and optional coating steps, the condom is removed from the mandrel, and optionally subjected to additional drying, further curing, and quality testing. Prior to packaging, the condoms are quality tested and rolled to form a cup-shaped elastic ring of predetermined size and circumference. At this point, additional lubricants, spermicides, bactericides, etc., may also be added to the condom. In this form, the condom is easily mountable for use during sexual intercourse by unrolling onto the penis.

Currently, condoms are manufactured under the Trojan Brand™ name, as well as other names with ribbed features. These ribbed features are typically made by dipping a mandrel with an etched surface into a latex bath. Latex deposits on the surface of the dipped mandrel to form the basic condom shape, while the latex that deposits in the etchings leaves behind a ribbed feature on the finished condom exterior.

However through trial and error, it has been determined that for a condom having a typical mid-point thickness of 0.075 mm, the maximum height that can be accomplished by the above mentioned technique is only about 0.1 mm or less. Such height usually does not provide much sensation to the condom user or partner. Attempting to make features with a greater height, through deeper etching of the condom mandrel, results in the formation of unacceptable weak spots on the condom. Broader (wider) raised patterns are also problematic. Latex tends to form a uniform coating in a broadly etched section of the mandrel rather than filling the void. This results in the pattern being lost once the condom is removed from the mandrel.

By using a grooved mandrel on which condoms are manufactured by a dip molding process, it is possible to produce condoms with ribs that are claimed to heighten stimulation during coitus. However, the ribs on such condoms produced by the known method are not effectively positioned or lack sufficient structural rigidity to produce effective clitoral and labial stimulation, and the production of pronounced ribbing by shaping of the mandrel weakens the structural integrity of the condom which is plainly unacceptable.

U.S. Pat. No. 6,182,661 to Solanki et al discloses a method for producing condom having monolithic projections to promote stimulation of clitoris. Specifically, Solanki et al. apply the projections between dips to a pre-deposited latex sheath. However such method substantially slows down the production speed, and the ability to manufacture a wider array of projections onto condoms is limited. Therefore, there remains a need for an efficient method of producing such condoms having projections greater than 0.1 mm in height to produce stimulation,

SUMMARY OF THE INVENTION

A method of manufacturing a condom comprising: 1) applying latex (as is or thickened with some agent) or another latex compatible vehicle directly to the surface of the condom mandrel to produce a raised pattern akin to bas relief; 2), drying the applied pattern, dipping the patterned mandrel in latex one or more times (over dip) to form a condom containing the raised pattern.

DETAILED DESCRIPTION OF THE INVENTION

Figure 1:
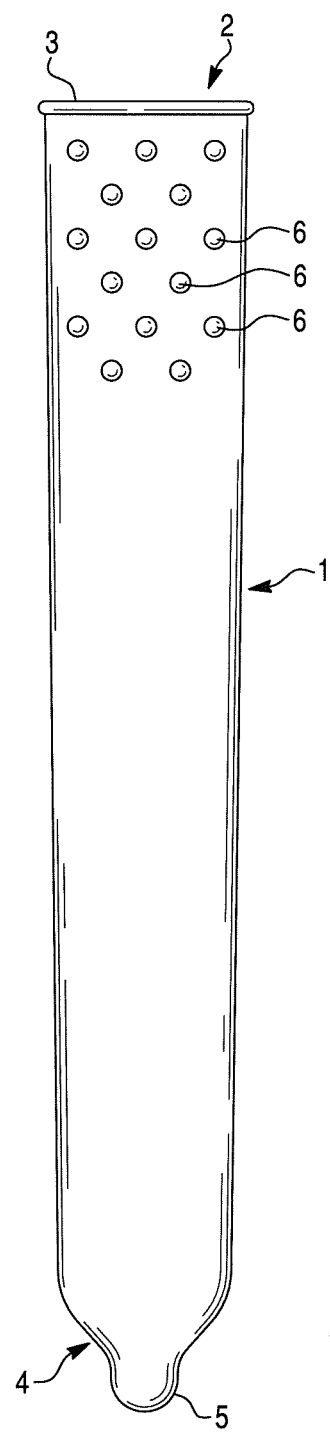
FIG. 1 is a plan view of a condom having a raised pattern in accordance with this invention.

In accordance with the invention there is provided a condom comprising a body having a closed end and an open end, and stimulation means between the ends of the condom for clitoral, labial, penile, or visual stimulation, the stimulation means comprising one or more projections (e.g. ribs, dots, rings, printed images, etc.). The stimulation means are formed by applying a pattern of coating onto a bare mandrel, drying the material, and then over-dipping the projections one or more times with a continuous film to complete the condom, wherein upon completion, the pattern coating material constitutes one or more projections. Upon completion of the condom dipping and curing, the condoms are removed from the mandrels using a series of brushes and air or water jets. Because of the adhesive nature of the non-tackified projections and the over dipped condom film, the projections adhere and become permanently attached to the overlying film and can be removed from the mandrel along with the condom as a permanent unity. Tactile projections as well as colored images can easily be perceived by the users due to the thin and transparent nature of the condom film compared to the much thicker projections.

Condoms of present invention are formed from natural rubber latex or solutions of synthetic material such as polyurethane. The specific type of material used to form the condom is not critical, although natural rubber latex is preferred.

Natural rubber latex is particularly useful in dipping operations, since, unlike synthetic rubber latex, such as chloroprene polymers (neoprene rubber), butadiene-styrene copolymers (Buna S rubber) or butadiene-acrylonitrile copolymers (Buna N rubber), natural rubber latex in its membranous form possesses a very high degree of wet film strength.

As used herein, the term "natural rubber" refers to elastomeric substances obtained from trees or plants such as the quayule and the hevea rubber trees usually by directly tapping the trees by means of cuts into the bark of the tree. The fluid that flows from the tree is not a part of the tree's sap but is natural rubber latex. The latex is made up of individual particles varying in size from between about 0.005 and 2.5 microns. Chemically the particles are stereoregular polymers of cis-1,4 polyisoprene carrying a negative charge with an isoelectric point in about pH of 4-5.

Natural rubber latex is subject to purification and coagulation within a few hours of collection unless a chemical stabilizer and/or preservative is added to the latex. As a practical matter, stabilizers and preservatives such as ammonia or combinations of ammonia and blends of secondary preservatives such as tetramethylthiuram disulfide, which also functions as a vulcanizer and accelerator, and zinc oxide are added directly to containers used in the collection of the latex.

The rubber content of the natural rubber latex as collected is usually between about 30 to 40 percent by weight. Generally, the latex is concentrated by one of several well-established methods, i.e., heat concentrating, centrifuging or creaming to produce latex having a rubber content of from about 60 to 75 percent for commercial use. The latex employed in the present invention has a rubber content ranging from about 35% to about 65% by weight.

In addition, as is well known in the art, reinforcing agents such as fumed silica and other materials, commonly known as "rubber chemicals", that impart particularly desired properties to the finished dipped goods may be added to the latex, i.e., curing, cross-linking or vulcanizing agents such as sulfur, vulcanization accelerators and activators, including metal oxides and hydroxides, i.e., zinc, calcium, sodium and organic accelerators such as the dithio carbamates, xanthates, thiourea, mercapto compounds, etc., antioxidants and other antidegradants in amounts that vary depending on characteristics of the latex, solids content, and properties desired.

The material applied directly to the condom mandrel to produce the raised pattern can be a thickened latex formulation, a heat-sensitive latex formulation, a silicone rubber, or another suitable polymeric material, each of which is optionally multi-colored. Suitable fillers as disclosed above can be used to thicken the material. The present over dip method allows the formation of raised patterns that are much higher and broader than have been previously commercially produced, such that the pattern heights ranging from greater than 0.1 to 0.9 mm and widths ranging to over 3 mm are now possible. In addition, latex tinted with pigment can be used to add color to the raised features, something that cannot be done by dipping of an etched mandrel. Furthermore, by applying various color thickened latex solutions to the condom mandrel prior to final condom dipping, condoms with multicolor raised spots, dots, stripes, rings, or images can be manufactured. The larger raised patterns have a greater likelihood of providing a novel physical sensation, while coloring adds an esthetic or visual appeal to the condom.

The projections are defined by a local increase in thickness of the condom material. According to one embodiment of the invention the stimulation means comprise a plurality of domelike studs, which may be arranged in a regular circumferential array. In another embodiment, the stimulation means comprises an elongate helical ridge. Multiple rings, spaced rings or C-shaped bands are also particularly useful as stimulating structures on the condom. The C-shaped bands are also advantageous as they allow the condom to be rolled and unrolled without binding when the roll hits the circumferential raised bead. The protrusion or protrusions massage and stimulate the clitoris and/or the penis during coitus and can serve as a visual and tactile indication that the condom is correctly oriented on the penis before and during intercourse.

Figure 2:
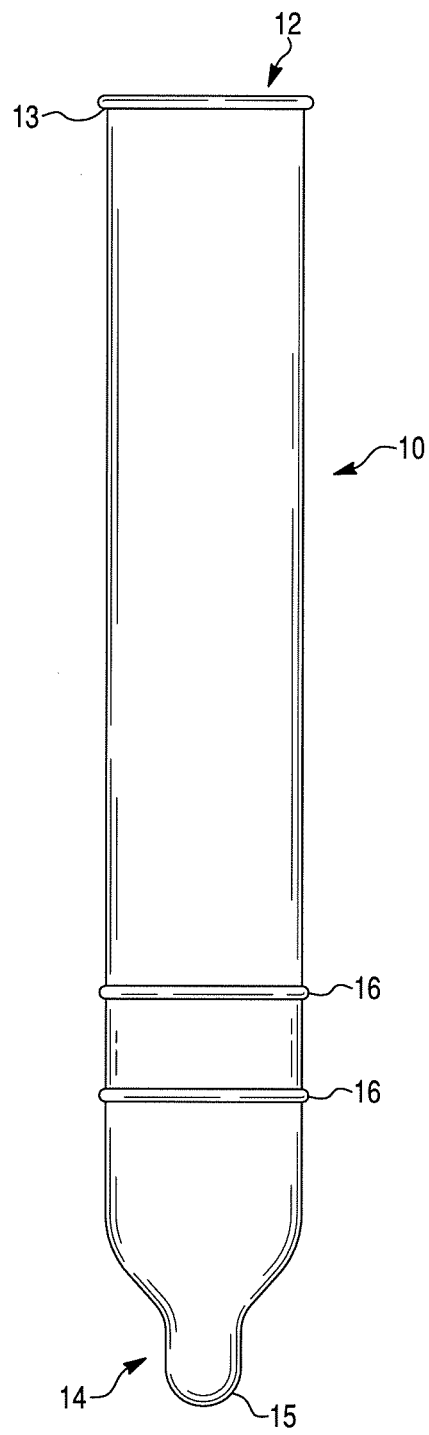
FIG. 2 is a plan view of a condom having an alternative raised pattern in accordance with this invention.

Projections may be applied to a variety of different mandrel shapes and not just to the so called straight wall shape illustrated in FIGS. 1 and 2. Such shapes include a tapered or flare shape where the diameter increases along the longitude of the condom from the minimum desired diameter at the open end to a larger diameter at the closed end. Another shape example is the bulbous end condom. This shape consists of two parallel sided sections having two different diameters and attach to each other with a truncated cone. The smaller diameter section is located at the open end to securely anchor the condom to the penis. The larger diameter section is located at the closed end for male comfort and stimulation. Other shaped mandrels may also be use to add novelty to the condom design.

The condom illustrated in FIG. 1 is of a generally conventional configuration. A cylindrical membrane 1 has an open end 2 provided with a conventional ring 3, which serves to retain the condom on the penis during coitus. The other end 4 of the membrane 1 is closed, and it has a centrally located bell-shaped nipple or teat 5.

The condom of FIG. 1 has a plurality of domelike studs, pips or knobbles 6 arranged in a regular circumferential array in the region of the open end of the condom, and confined to a minor part of the condom length. The studded area may be located anywhere along the length of the condom, but is immediately adjacent the open end of the condom shown in FIG. 1 as an example only. As shown, the studs are arranged in six circumferential rows of studs with the studs in each row equally spaced apart at a distance in the range of 10 mm to 20 mm, e.g. at 15 mm. The rows are spaced apart along the condom at a constant pitch in the range of 5 mm to 15 mm, preferably about 10 mm. Adjacent rows of studs 6 are circumferentially offset by half the distance between adjacent studs in the same row. It will be appreciated that different numbers of studs per row and different numbers of rows are possible. For example, the number of rows could be as few as three or as many as ten or more. Also, the studs could be arranged in different arrays, either regular or irregular.

The condom illustrated in FIG. 2 is of a generally conventional configuration as the condom shown in FIG. 1. A cylindrical membrane 10 has an open end 12 provided with a conventional ring 13, which serves to retain the condom on the penis during coitis. The other end 14 of the membrane 10 is closed, and has an essentially located bell-shaped nipple 15.

The condom of FIG. 2 has a different configuration of projections, which form the stimulation means of the present invention. Thus, the condom of FIG. 2 has a plurality of spaced rings 16 which circumscribe the membrane 10. The rings 16 may be located anywhere along the length of the condom and the placement of the rings 16 as shown in FIG. 2 is for exemplary purposes only. Further, the number of rings 16 can range from 1 to 20 or more, and can be evenly spaced or variably spaced along the length on the condom membrane 10. Importantly, the heights and widths of rings 16 are greater than achieved by processes of condom formation in which the condom mandrel is engraved as above discussed.

Figure 3:
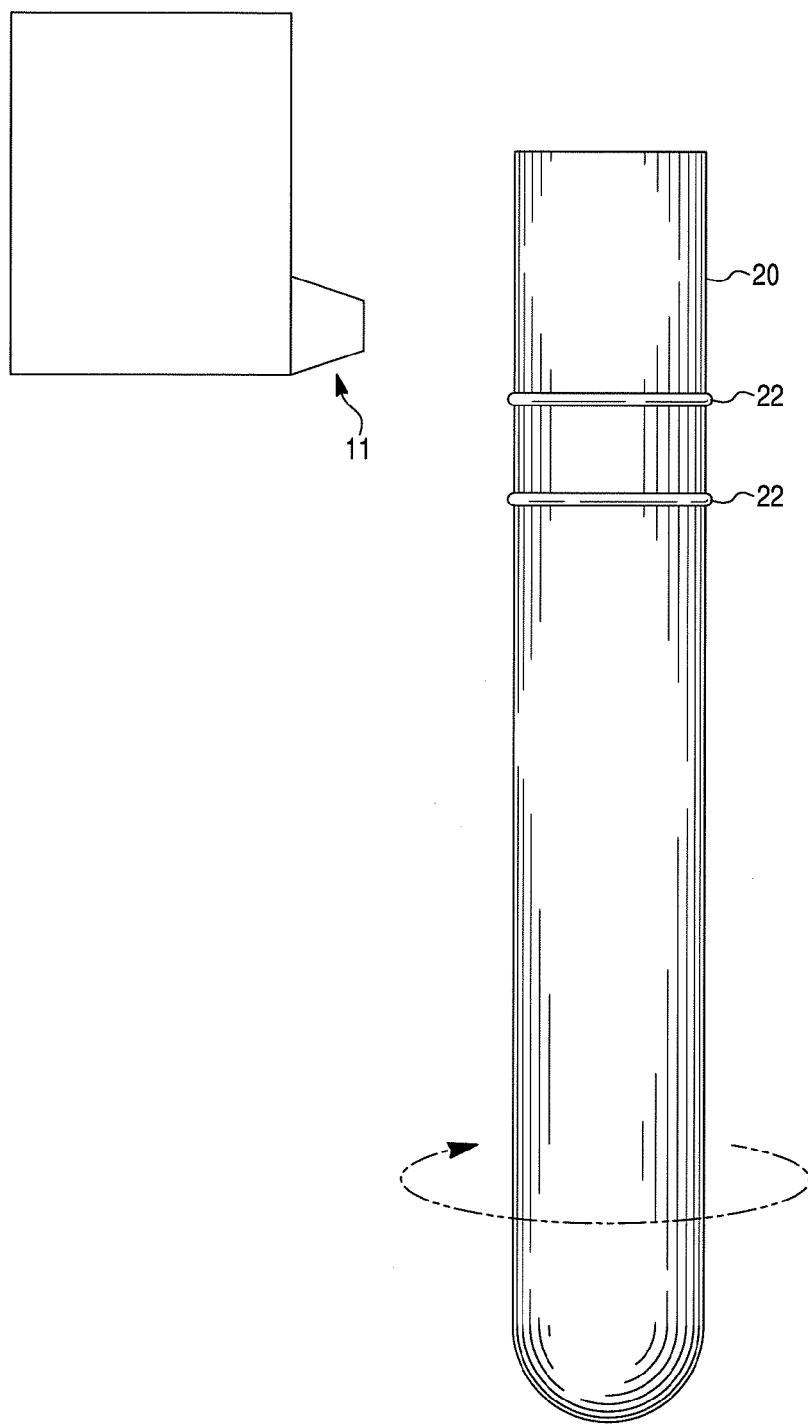
FIG. 3 is a schematic illustration of the initial steps of the condom manufacturing process used to form the condom of FIG. 2.
Figure 4:
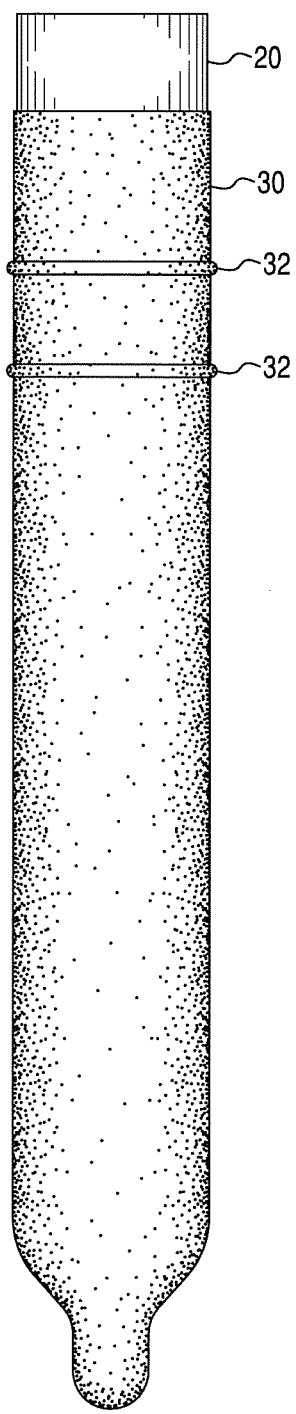
FIG. 4 is a schematic illustration of the final steps of the condom manufacturing process used to form the condom of FIG. 2.

FIGS. 3 and 4 depict a schematic illustration of the preferred method of manufacturing the condom of the invention. The condoms are manufactured by a dip molding process in which a conventionally shaped mandrel 20 is dipped into one or more liquid baths of latex or liquid polyurethane. Before the dips, a dispensing nozzle 11 coats a bare mandrel along its longitudinal axis with a relative viscous material (e.g. thickened latex), by the way of pulsing to produce studs, silk screening, rotogravure, or continuous flowing to form bands 22 as shown in FIG. 3. The nozzle can be advanced along the mandrel or the mandrel rotated as required and as shown in FIG. 3. As shown in FIG. 4, the coated mandrel is subsequently dipped into a liquid bath, and the studs or bands 22 are overcoated to form the condom sheath 30 which includes raised bands 32 that are equivalent to the patterns (22) on the mandrel 20. When set, the viscous material may be harder or softer than the material forming the body of the condom. In either case, the material should be rigid enough to retain its shape and provide a firm protrusion for effective clitoral stimulation and/or increased penile stimulation, or a visual cue. More than one dispensing nozzle or press may be utilized to expedite the application of the material on the mandrel. Once dried and set, the condom, including the material applied directly to the mandrel to form the projections, is removed from the mandrel as a unity.

Depending on the form, height, width, and length of the protrusions forming the stimulation means, there is the possibility that their presence may impede the donning of the rolled condom. This is particularly true of continuous circumferential rings. By applying the protrusions as a discontinuous circumferential bead, or C-shape, donning of the condom by unrolling over the protrusions is not problematic or uncomfortable to the male user. The protrusion or protrusions massage and stimulate the clitoris and/or the penis during coitus and can serve as a visual and tactile indication that the condom is correctly oriented on the penis before and during intercourse.

EXAMPLE

Three tumble loads (approximately 24,000-60,000 condoms per load) of Trojan® Magnum® style condoms, having two and three C-shaped raised ribs, were prepared using the over dip method described above. The dip line was operated in normal production fashion and within validated operating parameters. Latex for the raised pattern was applied to glass mandrels using nozzles fed via pressurized cylinders between 30-90 psi. The C-shaped ribs were made from Revertex® latex, thickened with the addition of fumed silica (Cab-O-Sil) at a preferred concentration of 2.0 to 3.5%, and colored violet with Flexiverse® Violet 23 dispersed pigment at a concentration of 0.3 to 0.7% by weight.

The application of the raised ribs of thickened latex to the glass condom mandrel was achieved using dispensing nozzles installed on a dip line, just downstream of the glass condom mandrel washing station. This location was approximately 8 feet from the entrance of the oven normally used to dry any remaining rinse water from the mandrels prior to the first dip. Mandrels were dried after washing and rinsing using an air knife and auxiliary heating. Feed tanks containing thickened latex were pressurized with compressed air. This pressure was used to force the latex through the feed lines and application nozzle(s). The raised ribs were formed by passing rotating mandrels beneath a continuous stream of thickened latex exiting the dispensing nozzle(s). The thickened latex is found to work best when applied to the bare mandrel at a viscosity range of 4000-30,000 cps and a temperature of 65-100° F. Mandrel rotation during thickened latex application was controlled in order to achieve a slight break of approximately 0.125 to 0.5 inches in the applied ring, resulting in a C-shaped deposition of thickened violet colored latex on the mandrel.

Modifications to the described embodiments further include, but not limited to, a plurality of axial or oblique ridges, a series of spaced circumferential ridges, or more than one helical ridge, could be applied in place of the double helical ridges. Also a combination of ridges and studs could be used, as well as other colored latex or images. However, the described embodiments are preferred because they are easier to apply than other formations. Subsequent over-dipping steps proceeded in accordance with standard dipping steps currently in practice for the production of standard condoms. The ease of incorporating equipment for application of the raised textures into current manufacturing lines is another advantage of using such a method for production. Alternate varieties of condoms can be manufactured through qualified minor changes at the "raised texture application station", which manifest themselves to unique condom types for the user with minimal line changeover downtime.

The invention claimed is:

1. A method for manufacturing a condom having an open end and a closed end, the method comprising the steps of coating a bare mandrel with a pattern of coating material, and subsequently uniformly applying additional material to said coated mandrel by dipping said coated mandrel into one or more baths of said additional material, drying the additional material and removing a formed condom from said mandrel, said formed condom having projections on the outside thereof matching said pattern of coating material, wherein said pattern and projections provides stimulation means between the ends of said completed condom.

2. A method according to claim 1, wherein a further uniform coating is applied to said mandrel after said additional material has been applied.

3. A method according to claim 1, wherein said mandrel is rotated about its longitudinal axis during said application of said pattern of coating material.

4. A method according to claim 1, wherein said pattern of coating material is applied in a continuous stream by dispensing means.

5. A method according to claim 4, wherein said dispensing means comprise one or more pressurized dispensing nozzles.

6. A method according to claim 4, wherein the dispensing means is moved relative to the longitudinal axis of said mandrel during said application of said pattern of coating material.

7. A method according to claim 1, wherein said pattern of coating material is applied in a series of discrete pulses by dispensing means.

8. A method according to claim 1, wherein said pattern of coating material comprises of at least one of thickened latex, a heat-sensitive latex formulation, a silicone rubber, or polymeric material.

9. A method according to claim 1, wherein said pattern is applied using silk screening or rotogravure.

10. A method according to claim 1, wherein said additional material is a rubber latex or polyurethane.

11. A method according to claim 1, wherein said additional material is natural rubber latex.

12. A method according to claim 1, wherein said stimulation means is in a raised form of at least one dot, image, band or ring.

13. A method according to claim 12, wherein said pattern of coating material is in the form of a plurality of continuous bands spaced along the surface of said mandrel.

14. A method according to claim 12, wherein said pattern of coating material is in the form of at least one C-shaped band.

15. A method according to claim 14, wherein said pattern of coating material is in the form of a plurality of C-shaped bands, spaced along the surface of said mandrel.

16. A method according to claim 1, wherein said stimulation means have a pattern height of at least 0.1 mm.

17. A method according to claim 1, wherein said pattern of coating material includes one or more pigments.

\* \* \* \* \*